United States Patent [19]
Greenlee et al.

[11] Patent Number: 4,576,748
[45] Date of Patent: Mar. 18, 1986

[54] 3-HYDROXY-3-AMINOETHYL β-LACTAMS

[75] Inventors: William J. Greenlee, Teaneck; Arthur A. Patchett, Westfield, both of N.J.

[73] Assignee: Merck & Co., Inc., Rahway, N.J.

[21] Appl. No.: 651,029

[22] Filed: Sep. 17, 1984

[51] Int. Cl.[4] ................. C07D 205/08; C07D 209/48; A61K 31/395
[52] U.S. Cl. ............................ 260/239 A; 548/477; 560/42; 560/159; 560/169
[58] Field of Search ..................................... 260/239 A

[56] References Cited
PUBLICATIONS

Ban, Chem. Abs. 96, 52566r, (1981).

Primary Examiner—Mark L. Berch
Attorney, Agent, or Firm—Hesna J. Pfeiffer; Daniels T. Szura

[57] ABSTRACT

β-Lactams of the formula:

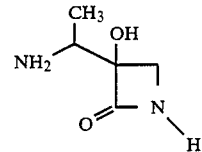

their preparation and use are disclosed.

3 Claims, No Drawings

3-HYDROXY-3-AMINOETHYL β-LACTAMS

BACKGROUND OF THE INVENTION

The invention is concerned with certain novel β-lactams having pharmaceutical utility.

Monocyclic β-lactams (monobactams) illustrated by the formula:

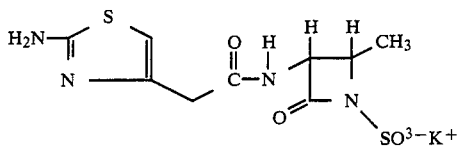

are a class of antibacterial agents [see e.g. Tetrahedron Letters 25, 887–880 (1984); Koster et al. "β-Lactam Antibiotics, Chemistry, and Biology"3, 339–375 (1982)].

Novel β-lactams having the formula:

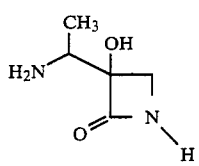

have been discovered.

SUMMARY OF THE INVENTION

Compounds of the formula:

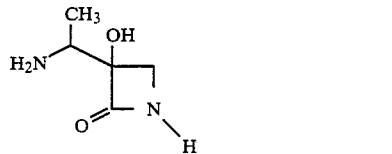

and their pharmaceutically acceptable salts.

DETAILED DESCRIPTION OF THE INVENTION

The present invention is embodied in compounds of the formula:

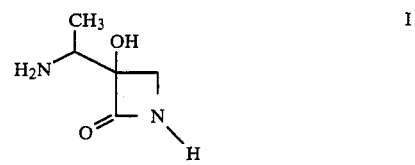

and their pharmaceutically acceptable salts.

The salts are generally acid addition products where the acid may be organic such as a sulfonic acid, a phosphonic acid, and the like or inorganic such as a hydrohalide, HCl, HBr, HI, a phosphorus acid e.g. phosphoric acid, $HNO_3$, $H_2SO_4$ and the like. The hydrohalide salt is preferred. The hydrochloride salt is especially preferred.

The compound of formula I will have antibacterial activity, for example against *Staphylococcus aureus* or *E. coli*, and will be useful to treat animals, especially humans.

The dosage for antibacterial treatment of patients in need of such treatment, will range from about 10 mg to about 2000 mg per day; the preferred dosage will be from about 500 mg to about 1500 mg per day; a more preferred dosage will be from about 500 mg to about 1000 mg per day.

The compounds may be administered either orally or parenterally using appropriate dosage forms. Suitable oral dosage forms are tablets, capsules, solutions, dispersions, elixers, and the like. Suitable parenteral dosage forms are fluid compositions such as emulsions, solutions, suspensions and the like. These dosage forms may be prepared using conventional procedures and will contain conventional pharmaceutically acceptable compounding ingredients.

The compounds of the present invention may be prepared by any convenient process. One such process is illustrated by the following set of equations:

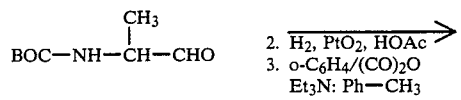
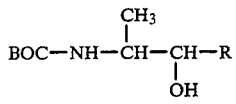

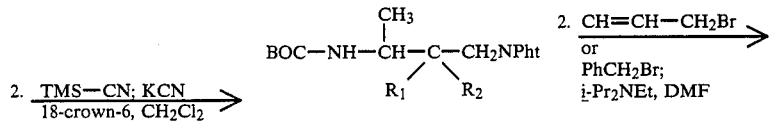

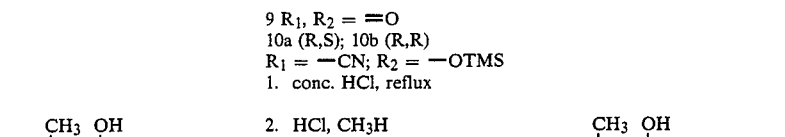
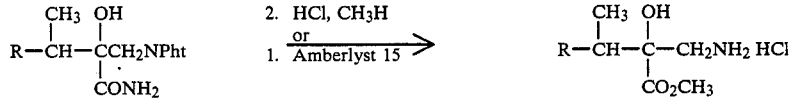

11a (R,S); 11b (R,R)  
R = —NH₂ HCl  
12a (R,S); 12b (R,R)  
R = —N(CH₂CH=CH₂)₂  
14a (R,S); 14b (R,R)  
R = —N(CH₂Ph)₂

CH₃OH, 60° C.  
2. NH₂NH₂, CH₃H 13 (R,S)  
R = —N(CH₂CH=CH₂)₂  
15a (R,S); 15b (R,R)  
R = —N(CH₂Ph)₂

1. t-BuMgCl, THF  
2. H₂; 30% Pd/(C)  
CH₃OH (R)₂N—C(CH₃)(OH)—C(H)—N(H)—C(=O)—

16 (R,S)  
R = —CH₂CH=CH₂  
17a (R,S); 17b (R,R)  
R = —CH₂Ph  
4a (R,S); 4b (R,R)  
R = —H

The formula I compound has two chiral centers and therefore exists in various stereoisomer forms. All of the stereoisomers are included, the preferred stereoisomers being the R,R and R,S forms.

The following example illustrates preparation of the formula I compound are as set out in the reaction equation above. All temperatures are °C. unless otherwise noted. The underlined numbers on the example correspond to the underlined numbers in the set of equations:

EXAMPLE 1

A. 3-t-BOC-amino-1-phthalimido-2-butanol (8)

A solution of N-t-BOC-(D)-alanine methyl ester (18.5 g; 0.090 mol) in ether (400 ml) was cooled (Dry-ice bath) as a cooled (−78° C.) solution (1M in hexane) of diisobutylaluminum hydride (200 ml; 0.20 mol) was added over 20 minutes. The mixture was stirred for 15 minutes and then quenched by careful addition of CH₃OH (50 ml) and then a saturated solution of Rochelle salt (60 ml). The mixture was allowed to warm to room temperature and the resulting gel was diluted with Rochelle salt solution (200 ml). The aqueous layer was extracted with ether and the combined organic portions were washed with H₂O and brine and dried (MgSO₄). The resulting solid aldehyde 5 (16.0 g showed a single spot on TLC (1:1 hexanes:EtOAc) $R_f$=0.60 and had an nmr spectrum (CDCl₃) identical to that reported for N-t-BOC-(L)-ananinal. Stanfield, C. F.; et al., *J. Org. Chem.*, 46, 4797 (1981). The crude aldehyde was combined immediately with KCN (5.91 g; 0.090 mol), HOAc (5.4 g; 0.090 mol) and CH₃OH (200 ml) and the solution was stirred overnight. The solvent was removed and the residue slurried with EtOAc and filtered. The cyanohydrin 6 remaining after evaporation showed two spots on TLC (40:1 CH₂Cl₂:CH₃OH) $R_f$=0.20, 0.25. A portion of this material (200 mg) was purified on silica gel, giving a white solid. NMR (CDCl₃): 1.27, 1.30 (3H, 2×d, J=7); 1.42 (9H,s); 3.8–4.1 (1H,m); 4.40, 4.50 (1H, 2×d, J=3,4); 4.8–5.1 (2H, broad). IR(CHCl₃): 3350, 2960, 2940, 1690, 1490 cm⁻¹. MS: m/e 201 (M⁺+1). A solution of the cyanohydrin 6 in HOAc (200 ml) was hydrogenated with PtO₂ (2 g) at 40 psi for 4 hrs. Removal of solvent in vacuo afforded crude aminoalcohol 7, which showed a single major spot on TLC (100:20:3:0.5 CHCl₃:CH₃OH:H₂O:HOAc) $R_f$=0.25. A mixture of 7 with phthalic anhydride (10.0 g; 0.067 mol), Et₃N (60 ml) and toluene (300 ml) was heated at reflux for 6 hrs while H₂O was removed with a Dean-Stark head. The residue after evaporation was taken up in EtOAc (250 ml) and extracted with HCl (0.5N), saturated aqueous NaHCO₃, H₂O and brine, and dried (MgSO₄). Evaporation of solvent and recrystallization of the resulting solid from EtOAc afforded alcohol 8 (10.6 g; 31.7 mmol; 35%) mp 140°–142° C. TLC (1:1 hexanes:EtOAc) $R_f$=0.40. NMR (CDCl₃): 1.25, 1.26 (3H, 2×d, J=7); 1.44, 1.46 (9H, 2×s); 3.1–3.2 (1H, broad); 3.6–3.9 (1H, m); 7.7–7.9 (4H, m).

IR (CHCl₃): 3440, 2950, 2935, 1765, 1700, 1495 cm⁻¹. MS: m/e 334 (M⁺). Anal. Calcd for C₁₇H₂₂N₂O₅: C, 61.06; H, 6.63; N, 8.38. Found: C, 61.25; H, 6.62; N, 8.13.

B. 3-t-BOC-amino-1-phthalimido-2-butanone

A solution of alcohol 8 (14.6 g; 43.7 mmol) in CH₂Cl₂ (150 ml) was added to a stirred suspension of CrO₃ (21.9 g) and pyridine (35.4 ml) in CH₂Cl₂ (300 ml). The mixture was stirred overnight and then decanted from insoluble tar. After evaporation of solvent, the residue was taken up in EtOAc and filtered. The filtrate was passed through silica gel (150 g) and solvent was removed, leaving a white solid. Recrystallization from hexanes-EtOAc gave ketone 9 (9.12 g; 27.5 mmol; 63%), mp 144°–146° C. NMR (CDCl₃): 1.25 (3H, d, J=7); 1.47 (9H, s); 4.5–4.6 (1H, m); 4.70 (2H, s); 5.1–5.3 (1H, broad); 7.8–8.0 (4H, m). IR (CHCl₃): 3430, 2950, 2925, 1775, 1710, 1490 cm⁻¹. MS: m/e 259 (M⁺-O-t-Bu). Anal. Calcd for C₁₇H₂₀N₂O₅: C, 61.43; H, 6.07; N, 8.43. Found: C, 61.40; N, 6.22; N, 8.25. $[\alpha]_D^{20}$=+68.3 (CH₃OH).

C. 3-t-BOC-amino-2-phthalimidomethyl-2-trimethysiloxybutyronitrile (10a, 10b)

A mixture of ketone 9 (2.42 g; 7.28 mmol) and trimethylsilylcyanide (0.97 ml; 7.28 mmol) in CH₂Cl₂ (10 ml) containing 10 mg each of KCN and 18-crown-6 was stirred for 2 hrs. Purification of the crude product by MPLC on silica gel (1:1 hexanes-EtOAc) gave the following: More-mobile diastereomer (10a) (2.010 g), mp 54°–56° C.

TLC: $R_f$=0.25. NMR (CDCl₃): 0.14 (9H, s); 1.29 (3H, d, J=7); 1.38 (9H, s); 4.02 (2H, s); 3.9–4.1 (1H, m); 4.70 (1H, broad d, J=8); 7.7–7.9 (4H, m).

IR (CHCl₃): 3430, 2960, 1780, 1720, 1500 cm⁻¹.

MS: m/e 431 (M⁺). Anal. Calcd for C₂₁H₂₉N₃O₅Si: C, 58.44; H, 6.77; N, 9.74. Found: C, 58.24; H, 7.03; N, 9.43. Less-mobile diastereomer (10b): TLC: $R_f$=0.30. NMR (CDCl₃): 0.20 (9H, s); 1.38 (3H, d, J=7); 1.42 (9H, s); 4.0–4.1 (1H, m); 4.05 (2H, AB, $J_{AB}$=14; $\delta_{AB}$=23); 4.70 (1H, broad d, J=9); 7.7–7.9 (4H, m). IR (CHCl₃): 3430, 2960, 1780, 1720, 1500 cm⁻¹. MS: m/e 431 (M⁺). Total yield=2,547 g (5.91 mmol; 81%).

D. 3-Amino-2-hydroxy-2-phthalimidomethylbutyramide hydrochloride (11a), 11b)

A solution of nitrile 10a (0.970 g) in concentrated HCl (25 ml) was allowed to stir at 5° C. for 18 hrs. Evaporation of the solvent and recrystallization of resulting solid from CH$_3$OH gave 11a, mp 205°–209° C. TLC (3:1:1:1 EtOAc:BuOH:HOAc:H$_2$O) R$_f$=0.50. NMR (D$_2$O): 1.62 (3H, d, J=7); 3.97 (1H, q, J=7); 4.27 (2H, AB, J$_{AB}$=15, δ$_{AB}$=36); 8.0–8.1 (4H, m).

A similar treatment of nitrile 10b (0.652 g) afforded 11b, mp 160°–162° C. TLC (3:1:1:1 EBAW) R$_f$=0.50. NMR (D$_2$O): 1.50 (3H, d, J=7); 3.98 (1H, q, J=7); 4.35 (2H, AB, J$_{AB}$=16, δ$_{AB}$=22); 8.2–8.3 (4H, m).

E. 3-Diallylamino-2-hydroxy-2-phtalimidomethylbutyramide (12a, 12b)

Nitrile 10a (0.281 g; 0.652 mmol) was treated with concentrated HCl as described above. The crude 11a was combined with allyl bromide (0.63 ml; 7.3 mmol), i-Pr$_2$NEt (0.57 ml; 3.3 mmol) and DMF (3.5 ml) and the mixture was stirred for 18 hrs. Purification of the product on silica gel (40:1 CH$_2$Cl$_2$:CH$_3$OH) and recrystallization from hexanes-EtOAc gave amide 12a (0.298 g; 8.34 mmol; 92%), mp 136°–140° C. TLC: R$_f$=0.60. NMR: 1.30 (3H, d, J=7); 3.24 (1H, q, J=7); 3.25 (4H, AB, J$_{AB}$=14; δ$_{AB}$=104; J$_{AB}$=4; J$_{BX}$=8); 4.12 (2H, AB, J$_{AB}$=13; δ$_{AB}$=122); 5.17 (2H, d, J=7); 5.20 (2H, d, J=19); 5.8–6.0 (2H, m); 7.7–7.9 (4H, m).

IR (CHCl$_3$): 3520, 3380, 2980, 2830, 1770, 1700, 1385 cm$^{-1}$. MS: m/e 358 (M$^+$+1). Anal. Calcd for C$_{19}$H$_{23}$N$_3$O$_4$: C, 63.85; H, 6.48; N, 11.76. Found: C, 63.67; H, 6.52; N, 11.62. Treatment of nitrile 10b (0.089 g; 0.21 mmol) as described above provided amide 12b, mp 176°–180° C. in 73% yield. TLC: R$_f$=0.60. NMR (CDCl$_3$: 1.29 (3H, d, J=7); 3.13 (4H, AB, J$_{AB}$=14; δ$_{AB}$=104; J$_{AX}$=4, J$_{BX}$=8); 3.13 (1H, q, J=7); 4.19 (2H, d, J=2); 5.00 (2H, d J=9); 5.14 (2H, d, J=19); 5.42 (1H, broad s); 5.6–5.8 (2H, m); 7.06 (1H, broad s); 7.7–7.9 (4H, m). IR (CHCl$_3$): 3520, 3380, 2980, 2830, 1770, 1700, 1380 cm$^{-1}$. MS: m/e 357 (M$^+$). Anal. Found: C, 63.53; H, 6.49; N, 11.64.

F. Methyl 2-aminomethyl-3-diallylamino-2-hydroxybutanoate hydrochloride (13)

A mixture of amide 12a (0.913 g; 2.55 mmol), amberlyst 15 resin (13.5 g) and CH$_3$OH (20 ml) was warmed at 60° C. for 7 days. The resin was rinsed with CH$_3$OH and then the product was eluted with 2:1 CH$_3$OH:ET$_3$N. Purification on silica gel (1:1 hexanes:ether) gave the phthalimido ester (0.633 g; 1.63 mmol; 63%) as a white solid. Recrystallization from hexanes gave material, mp 92°–94° C. NMR (CDCl$_3$): 1.23 (3H, d, J=7); 1.60 (s, H$_2$O); 3.12 (4H, ABX, J$_{AB}$=14, δ$_{AB}$=124; J$_{AX}$=4; J$_{BX}$=8); 3.22 (1H, q, J=7); 3.84 (3H, s); 3.95 (2H, d, J=2); 5.07 (2H, d, J=20); 5.09 (2H, d, J=12); 5.6–5.8 (2H, m); 7.7–7.9 (4H,m).

IR (CHCl$_3$): 3500, 2980, 2960, 2830, 1780, 1720, 1430, 1400 cm$^{-1}$. MS: m/e 313 (M$^+$—CO$_2$CH$_3$). Anal. Calcd for C$_{20}$H$_{24}$N$_2$O$_5$: C, 64.50; H, 6.50; N, 7.52. Found: C, 64.46; H, 6.49; N, 7.72. This ester (0.441 g; 1.19 mmol) was treated with anhydrous hydrazine (75.9 mg; 2.37 mmol) in CH$_3$OH (4 ml). After 15 minutes, solvent was removed and the residue combined with HOAc (0.22 ml; 3.81 mmol) and CH$_3$OH (4 ml). This mixture was stirred for 24 hours and then filtered to remove phthalhydrazide. The crude aminoester was purified on silica gel (100:20:3:0.5 CMWA), then reconcentrated from CH$_3$OH-HCl ($\frac{1}{2}$-saturated), affording 13 (0.292 g; 0.928 mmol; 78%). TLC: R$_f$=0.20. NMR (CD$_3$OD): 1.53 (3H, d, J=7); 2.42 (2H, AB, J$_{AB}$=12, δ$_{AB}$=42); 3.7–4.0 (2H, m); 4.00 (3H, s); 4.23 (1H, q, J=7); 5.65 (2H, d, J=10); 5.67 (2H, d, J=18); 5.9–6.2 (2H, m).

G. 3-(1-Diallylamino)ethyl-3-hydroxy-2-azetidinone (16)

To a suspension of aminoester 13 (0.249 g; 0.790 mmol) in THF (2.5 ml) was added a solution (2.8M in ether) of ethylmagnesium bromide (1.69 ml; 4.74 mmol). The mixture was stirred for 3 hours., then diluted with saturated NaHCO$_3$ solution and extracted with EtOAc. The crude product was purified on silica gel (ether), giving 16 (90.0 mg; 0.429 mmol; 54%) as a white solid. Recrystallization from CH$_3$OH gave crystals, mp 115°–117° C. TLC: R$_f$=0.40. NMR (CDCl$_3$): 1.11 (3H, d, J=7); 3.10 (4H, ABX, J$_{AB}$=15, δ$_{AB}$=40, J$_{AX}$=5, J$_{BX}$=8); 3.0–3.2 (1H, m); 3.44 (2H, AB, J$_{AB}$=6; δ$_{AB}$=66); 4.21 (2H, d, J=10), 4.24 (2H, d, J=19); 5.6–5.8 (2H, m); 5.9–6.1 (1H, broad s). IR (CHCl$_3$): 3430, 3400–3100, 2980, 2840, 1765 cm$^{-1}$. MS: m/e 169 (M$^+$-allyl). Anal. Calcd for C$_{11}$H$_{18}$N$_2$O$_2$: C, 62.83; H, 8.63; N, 13.32. Found: C, 63.09; H, 8.70; N, 13.14.

H. 3-Dibenzylamino-2-hydroxy-2-pthalimidomethylbutyramide (14a, 14b)

Ketone 9 (9.0 g; 27.1 mmol) was treated as described above with trimethylsilylcyanide (4.6 ml; 33.9 mmol), KCN (20 mg), 18-crown-6 (20 mg) in CH$_2$Cl$_2$ (50 ml). The crude product was taken up in concentrated HCl (300 ml) and stirred for 18 hours at 5° C. Evaporation and reconcentration from CH$_3$OH gave amides 11a, 11b as a white solid. This was combined with benzyl bromide (29 ml; 0.244 mol) and i-Pr$_2$NEt (16.6 ml; 94.8 mmol) in DMF (100 ml). The mixture was stirred for 48 hours and then evaporation to dryness in vacuo. A solution of residue in EtOAc was extracted with H$_2$O and brine and dried (MgSO$_4$). The crude product was chromatographed on silica gel (200 g) in ether to remove excess benzyl bromide. The resulting white foam was purified by MPLC (ether), giving the following: More-mobile diastereomer (14a; 4.14 g). TLC: R$_f$=0.40. NMR (CDCl$_3$): 1.40 (3H, d, J=7); 1.67 (s, H$_2$O); 3.21 (1H, q, J=7); 3.74 (4H, AB, J$_{AB}$=12; δ$_{AB}$=132); 4.12 (2H, AB, J$_{AB}$=14; δ$_{AB}$=122); 5.73 (1H, s); 7.2–7.4 (12H, m); 7.7–7.9 (4H, m). IR (CHCl$_3$): 3520, 3400, 2980, 2850, 1775, 1700, 1385 cm$^{-1}$. MS (FAB): m/e 458 (M$^+$+1). Less-mobile diastereomer (14b; 0.850 g): TLC: R$_f$=0.35. NMR (CDCl$_3$); 1.48 (3H, d, J=7); 1.67 (s, H$_2$O); 2.89 (1H, q, J=7); 3.29 (2H, d, J=14); 3.7–3.9 (2H, broad s); 3.98 (2H, AB, J$_{AB}$=14; δ$_{AB}$=58); 5.54 (1H, broad s); 6.07 (1H, broad s); 6.8–7.74 (10H, broad); 7.7 (4H, s). IR (CHCl$_3$): 3520, 3400, 3000, 2850, 1775, 1710, 1575, 1390, 1360 cm$^{-1}$. MS (FAB): m/e 458 (M$^+$+1).

Anal. Calcd for C$_{27}$H$_{27}$N$_3$O$_4\frac{1}{2}$H$_2$O: C, 69.51; H, 6.05; N, 9.01. Found: C, 69.66; H, 5.74; N, 8.86. Total yield=4.99 g (10.9 mmol; 40%).

I. Methyl 2-aminomethyl-3-dibenzylamino-2-hydroxybutanoate hydrochloride (15a, 15b)

Amide 14a (1.95 g; 4.27 mmol) was combined with 5 concentrated HCl and the mixture was heated at reflux for 18 hours. The residue after evaporation was dissolved in CH₃OH (50 ml) and the solution saturated with anhydrous HCl. After 48 hours, the solution was evaporated, giving the product as a white foam. Purification on silica gel (100:20:3:0.5 CMWA) and reconcentration from HCl-CH₃OH (half-saturated) afforded 15a as a hygroscopic white solid (1.26 g; 3.04 mmol; 71%). TLC: $R_f = 0.25$.

NMR (D₂O): 1.63 (3H, d, J=7); 3.36 (2H, AB, $J_{AB}=15$; $\delta_{AB}=36$); 3.50 (3H, s); 3.93 (1H, q, J=7); 4.54 (4H, AB, $J_{AB}=15$; $\delta_{AB}=107$); 7.4–7.6 (10H, broad s). Amide 14b (0.650 g; 1.42 mmol) was treated as described above, affording aminoester 15b (0.379 g; 0.914 mmol; 64%) as a hygroscopic white solid. TLC: $R_f=0.25$. NMR (D₂O): 1.51 (3H, d, J=7); 3.27 (2H, AB, $J_{AB}=14$; $\delta_{AB}=40$); 3.68 (1H, q, J=7); 3.92 (3H, s); 4.32 (4H, AB, $J_{AB}=13$; $\delta_{AB}=61$); 7.4–7.6 (10H, broad s).

J. 3-(1-Dibenzylamino)/ethyl-3-hydroxy-2-azetidinone (17a, 17b)

Aminoester hydrochloride 15a (1.26 g; 3.04 mmol) was suspended in THF (10 ml) and cooled (0° C.) as a solution (2M in THF) of t-butylmagnesium chloride (9.1 ml; 18.2 mmol) was added. The mixture was stirred for 18 hours and then quenched with saturated NH₄Cl solution. The aqueous layer was extracted with EtOAc and the combined organic portions were washed with saturated NH₄Cl, H₂O and brine, and dried (Na₂SO₄). Purification of the product on silica gel (ether) gave 17a (0.500 g; 1.61 mmol; 53%). Recrystallization from hexanes-EtOAc gave crystalline lactam, mp 149°–151° C. TLC: $R_f=0.30$. NMR (CDCl₃): 1.21 (3H, d, J=7); 1.59 (s, H₂O); 3.25 (1H, q, J=7); 3.44 (2H, AB, $J_{AB}=5$, $\delta_{AB}=76$; 3.59 (4H, AB, $J_{AB}=12$; $\delta_{AB}=48$); 5.21 (1H, broad s); 5.77 (1H, broad s); 7.2–7.4 (10H, m), IR (CHCl₃): 3440, 3400–3150; 2980, 2820, 2720, 1765 cm⁻¹. MS: m/e 267 (M+—NH—C=O). Anal. Calcd for c₁₉H₂₂N₂O₂: C, 73.52; H, 7.14; N, 9.03. Found: C, 73.42; H, 7.26; N, 8.72. Similar treatment of aminoester hydrochloride 15b (0.111 g; 0.268 mmol) provided 17b (67.5 mg; 0.218 mmol; 81%) mp 145°–147° C. TLC: $R_f=0.25$. NMR (CDCl₃): 1.22 (3H, d, J=7): 3.05 (1H, q, J=7); 3.21 (2H, AB, $J_{AB}=6$, $\delta_{AB}=36$); 3.77 (4H, AB, $J_{AB}=14$; $\delta_{AB}=180$); 6.14 (1H, broad s); 7.2–7.5 (10H, broad s). IR (CHCl₃): 3440, 3400–3150, 2980, 2850, 2720, 1760 cm⁻¹. MS: m/e 414 (M+- —NH—C=O). Anal. Found: C, 73.12; H, 7.14; N, 8.92.

K. 3-(1-Aminoethyl)-3-hydroxy-2-azetidinone (4a)

Lactam 17a (41 mg; 0.132 mmol) was dissolved in CH₃OH (2 ml) and 0.1N HCl (1 ml) and hydrogenated with 25 mg of 30% Pd(C) at 40 psi for 18 hrs. The product was purified on DOWEX 50W-X4 (2 g) with 0.5N NH₄OH as eluant. The resulting solid (13.9 mg; 0.107 mmol; 81%) was recrystallized from CH₂Cl₂—CH₃OH, mp 112°–115° C. TLC (3:1:1:1 EBAW) $R_f=0.30$. NMR (CD₃OD): 1.13 (3H, d, J=7); 3.12 (1H, q, J=7); 3.27 (2H, AB, $J_{AB}=6$; $\delta_{AB}=58$). MS: m/e 131 (M++1). Anal. Calcd for C₅H₁₀N₂O₂·¼C-H₃OH: C, 45.64; H, 8.03; N, 20.27. Found: C, 45.66; H, 7.68; N, 20.70. Similar treatment of lactam 17b (53 mg; 0.17 mmol) afforded 4b as a white solid (17 mg; 0.13 mmol; 75%). TLC (3:1:1:1 EBAW) $R_f=0.30$. NMR (1N DCl in D₂O): 1.45 (3H, d, J=7); 3.54 (2H, AB, $J_{AB}=7$; $\delta_{AB}=32$); 3.83 (1H, q, J=7). MS: m/e 131 (M++1).

X-ray Crystal Structure Analysis of 12a hydrochloride salt (recrystallized from CH₃OH)

Space group C2; Cell Constants: a=23.764(3)°A; b=5.563(1)°A; c=9.576(1)°A; β=108.32(1)°. 907 reflections measured, 889 reflections observed (I 3σI); Cu$_\alpha$K radiation, R=0.035. Tables of atomic coordinates, bond distances and angles and thermal parameters have been deposited with the Cambridge Crystallographic Data Centre, Cambridge, England.

Claims to the invention follow.

What is claimed is:

1. A compound having the formula

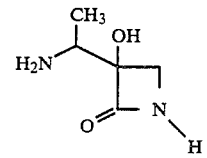

and its pharmaceutically acceptable salts.

2. The R,R isomer of the claim 1 compound.
3. The R,S isomer of the claim 1 compound.